(12) United States Patent
Oosawa et al.

(10) Patent No.: US 8,009,936 B2
(45) Date of Patent: Aug. 30, 2011

(54) CASE IMAGE SEARCH APPARATUS AND SYSTEM

(75) Inventors: Akira Oosawa, Tokyo (JP); Takayuki Udagawa, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 822 days.

(21) Appl. No.: 12/058,748

(22) Filed: Mar. 30, 2008

(65) Prior Publication Data

US 2008/0240494 A1 Oct. 2, 2008

(30) Foreign Application Priority Data

Mar. 30, 2007 (JP) ................................. 2007-095439

(51) Int. Cl.
*G06K 9/32* (2006.01)

(52) U.S. Cl. ......... 382/305; 382/128; 382/154; 382/282

(58) Field of Classification Search .................. 382/128, 382/131, 132, 154, 282, 305
See application file for complete search history.

(56) References Cited

U.S. PATENT DOCUMENTS

| 6,804,683 | B1 | 10/2004 | Matsuzaki et al. | |
|---|---|---|---|---|
| 7,188,103 | B2 | 3/2007 | Furuhashi et al. | |
| 7,421,103 | B2 * | 9/2008 | Thesen | 382/131 |
| 7,427,200 | B2 * | 9/2008 | Noble et al. | 434/274 |
| 7,486,812 | B2 * | 2/2009 | Gurcan et al. | 382/131 |
| 7,603,165 | B2 * | 10/2009 | Townsend et al. | 600/427 |
| 7,634,048 | B2 * | 12/2009 | Kojima et al. | 378/19 |

FOREIGN PATENT DOCUMENTS

| JP | 2001-101449 A | 4/2001 |
|---|---|---|
| JP | 2001-155019 A | 6/2001 |
| JP | 2004-164503 A | 6/2004 |

* cited by examiner

*Primary Examiner* — Yosef Kassa
(74) *Attorney, Agent, or Firm* — Sughrue Mion, PLLC

(57) ABSTRACT

An arbitrary cross-sectional image (MPR image) is used as an image for searching a case DB which has registered case images for a case image similar to an image to be diagnosed. A user terminal produces an axial image with reference to a diseased site in the MPR image, the axial image containing the diseased site, calculates a feature value (first feature value) of the diseased site contained in the axial image, and sends the feature value to the case DB. A case image server compares the received first feature value with a feature value (second feature value) for each case registered in a feature value DB, searches the case DB for a case image having a second feature value similar to the first feature value based on the comparison result, and sends the searched case image to the user terminal.

13 Claims, 12 Drawing Sheets

AXIAL IMAGE

CROSS SECTION ACTUALLY USED AS QUERY (AXIAL CROSS SECTION)

ARBITRARY CROSS SECTION SPECIFIED BY USER (MPR)

FIG.6
QUASI-CIRCLE 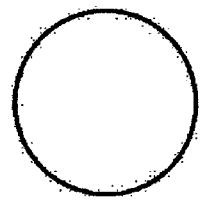 LOBULAR SHAPE 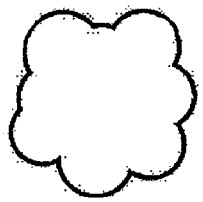 POLYGON 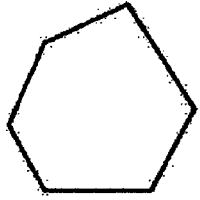 STAR 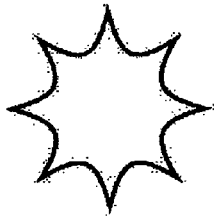
SPICULAR SHAPE 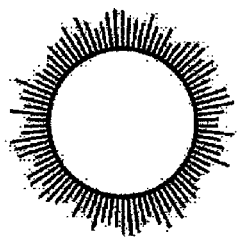 SAWTOOTH SHAPE 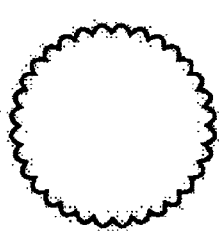
FIG.7
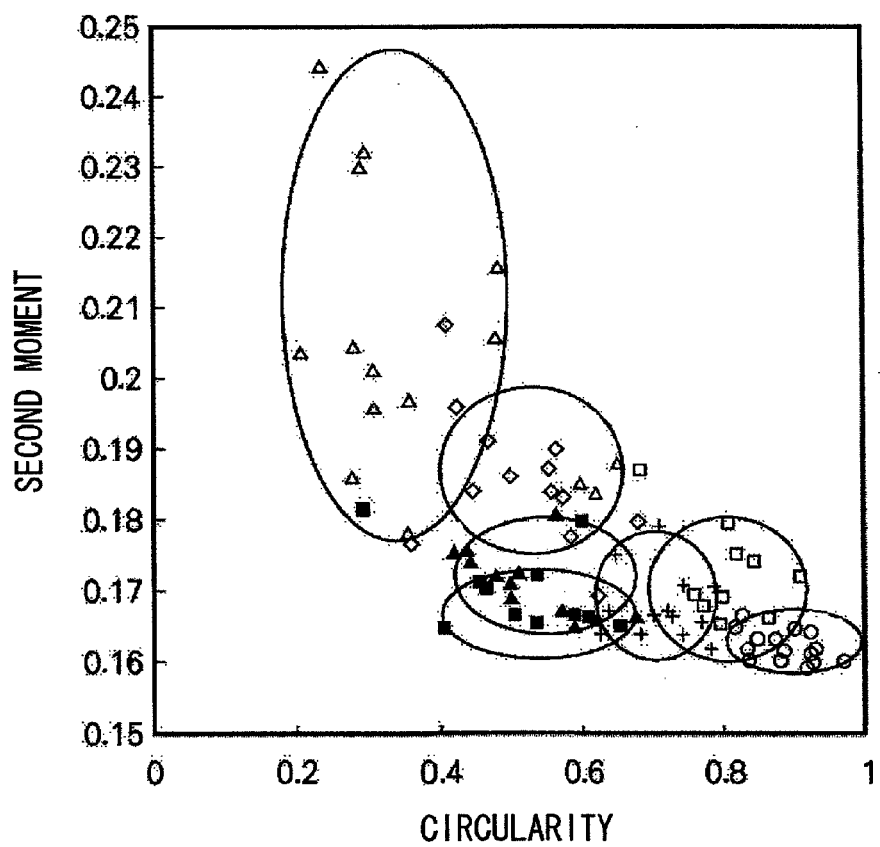

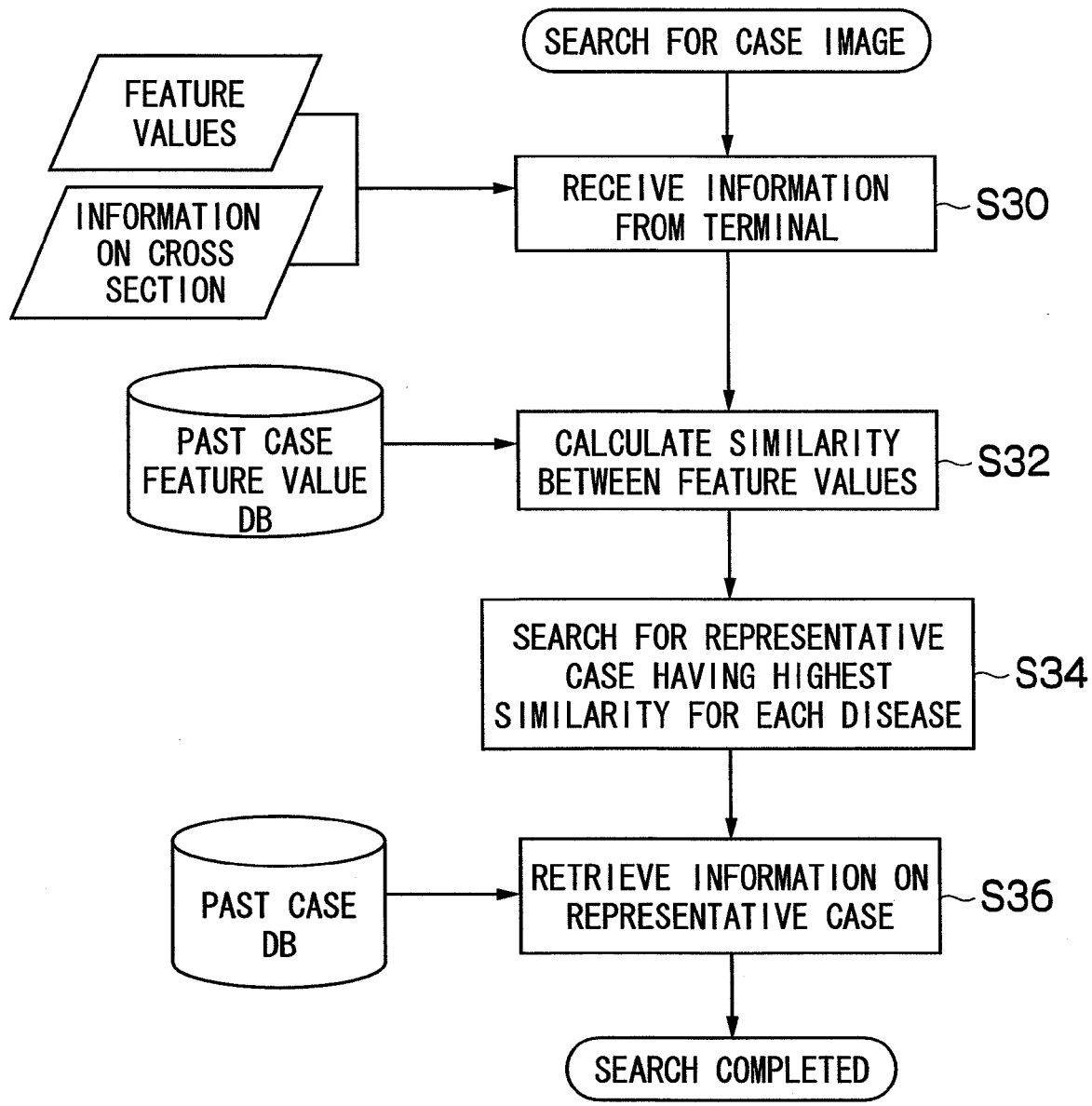

FIG.11

|  | FEATURE VALUE $m_1$ | FEATURE VALUE $m_2$ | ... | FEATURE VALUE $m_n$ |
|---|---|---|---|---|
| QUERY | 2.245 | 1.202 | ... | 1.98 |

FIG.12

| CASE ID | FEATURE VALUE $M_1$ | FEATURE VALUE $M_2$ | ... | FEATURE VALUE $M_n$ |
|---|---|---|---|---|
| A-001 | 1.635 | 1.211 | ... | 2.28 |
| A-002 | 1.492 | 1.275 | ... | 4.66 |
| ⋮ | ⋮ | ⋮ | ⋮ | ⋮ |

| CASE ID | FEATURE VALUE $M_1$ | FEATURE VALUE $M_2$ | ... | FEATURE VALUE $M_n$ |
|---|---|---|---|---|
| B-001 | 3.665 | 0.002 | ... | 4.1 |
| B-002 | 3.558 | 0.508 | ... | 3.8 |
| ⋮ | ⋮ | ⋮ | ⋮ | ⋮ |

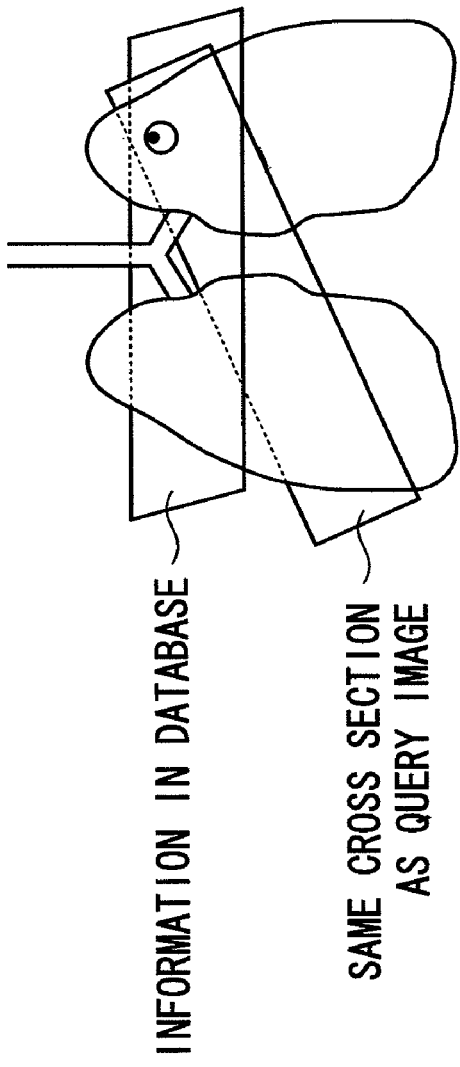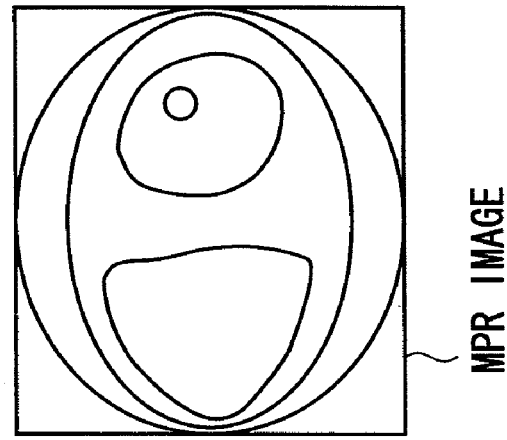
FIG.16A
FIG.16B
INFORMATION IN DATABASE
SAME CROSS SECTION AS QUERY IMAGE
MPR IMAGE

CASE IMAGE SEARCH APPARATUS AND SYSTEM

BACKGROUND OF THE INVENTION

1. Field of the Invention

The present invention relates to a case image search apparatus and system, particularly to a technology for using a feature value extracted from a query image to search for a case image similar to the query image.

2. Description of the Related Art

A method for searching for a three-dimensional model has been proposed (Japanese Patent Application Laid-Open No. 2004-164503). The method includes the steps of extracting a feature value (first feature value) from a two-dimensional image that will be a search key, generating a plurality of two-dimensional images by viewing a three-dimensional model to be searched for from different points of view, extracting a feature value (second feature value) from each of the plurality of two-dimensional images, using the first and second feature values to carry out similarity searching, and searching for a three-dimensional model similar to the search key.

An apparatus for searching for a similar image has also been proposed (Japanese Patent Application Laid-Open No. 2001-155019). The apparatus sets part of a three-dimensional image to be diagnosed as a region of interest, extracts a feature value from the region of interest, compares the extracted feature value with feature values of images in a database to calculate similarities, and selects similar images from the database based on the calculated similarities in descending order of similarity.

Further, an apparatus for displaying a three-dimensional image has been proposed (Japanese Patent Application Laid-Open No. 2001-101449). The apparatus sets a plane in an image three-dimensional voxel space with reference to a three-dimensional image displayed after arbitrarily rotated and moved, and uses the pixel values of the voxels that interest the plane to create an MPR image. It is therefore possible to easily display an MPR image arbitrarily angled and positioned and intuitively understand the positional relationship between the MPR image and the three-dimensional image.

The three-dimensional model search method described in Japanese Patent Application Laid-Open No. 2004-164503 requires preparing a plurality of second feature values used for searching for one three-dimensional model in advance (feature values extracted from a plurality of two-dimensional images obtained by viewing a three-dimensional model from different points of view). Therefore, in particular, when the direction of the two-dimensional image that will be the search key (the direction of the line of sight) is not established, it is necessary to prepare the second feature values for all possible directions of the line of sight. Further, when a large number of three-dimensional models will be searched for, it is difficult to prepare the second feature values.

The similar image detection apparatus descried in Japanese Patent Application Laid-Open No. 2001-155019 cannot search a database for a two-dimensional image similar to a reference two-dimensional image or a three-dimensional image containing the reference two-dimensional image therein.

The three-dimensional image display apparatus described in Japanese Patent Application Laid-Open No. 2001-101449 is not designed to search an image database for an image or display a searched image, and hence no screen interface is considered, for example, for searching for a similar case.

SUMMARY OF THE INVENTION

The present invention has been made in view of such circumstances. An object of the present invention is to provide a case image search apparatus and system that can search case images registered in a database for a similar case image based on an arbitrary cross-sectional image of a three-dimensional image to be diagnosed.

To achieve the above object, the case image search apparatus according to a first aspect of the present invention comprises: a cross-sectional image specifying device which specifies an arbitrary cross-sectional image obtained by cutting a three-dimensional image to be diagnosed with a cutting plane arbitrarily positioned and angled; a cross-sectional image producing device which produces a cross-sectional image from the three-dimensional image with reference to a diseased site in the specified arbitrary cross-sectional image, the cross-sectional image oriented in an axial direction set in advance and containing the diseased site; a feature value calculating device which calculates a first feature value of the diseased site contained in the produced cross-sectional image based on the cross-sectional image; a database which stores a plurality of case images and a second feature value of each of the case images, which is associated with a case image, the second feature value for diseased site in a cross-sectional image oriented in the axial direction set in advance; and a searching device which compares the first feature value with the second feature value and searches the database for a case image having a second feature value similar to the first feature value.

An arbitrary cross-sectional image (MPR image) is prepared in such a way that it can be used as a search image for searching a database which stores case images for a case image similar to an image to be diagnosed. That is, with reference to a diseased site in the arbitrary cross-sectional image, a cross-sectional image containing the diseased site and oriented in an axial direction set in advance (an axial image, for example) is produced from the three-dimensional image. Then, a first feature value of the diseased site contained in the produced cross-sectional image is calculated based on the cross-sectional image. On the other hand, the database which stores a plurality of case images and a second feature value of each of the case images, which is associated with a case image, the second feature value for diseased site in a cross-sectional image oriented in the axial direction set in advance (an axial image, for example). By comparing the first feature value with the second feature value, the database is searched for a case image having a second feature value similar to the first feature value.

That is, since an arbitrary cross-sectional image (MPR image) can be used as the search image (query image) and the arbitrary cross-sectional image is converted into a cross-sectional image oriented in an axial direction set in advance (an axial image, for example) to calculate the first feature value, the database only needs to hold the second feature value of a diseased site in a cross-sectional image oriented in the axial direction set in advance (an axial image, for example).

According to a second aspect of the present invention, in the case image search apparatus according to the first aspect, the database stores each of the case images as a three-dimensional image, and the case image search apparatus further includes: a first cross-sectional image producing device which produces a first arbitrary cross-sectional image from the three-dimensional image based on the specification by the cross-sectional image specifying device; a first displaying device which displays the produced first arbitrary cross-sectional image; a second cross-sectional image producing device which produces a second arbitrary cross-sectional image from the three-dimensional image corresponding to the case image searched for by the searching device, the second arbitrary cross-sectional image containing a diseased site and angled by the same amount as that specified by the cross-sectional image specifying device; and a second display device which displays the produced second arbitrary cross-sectional image.

In this way, the second arbitrary cross-sectional image (case image to be referred to) angled by the same amount as the first arbitrary cross-sectional image to be diagnosed can be displayed. Since a three-dimensional image to be diagnosed can be displayed as an arbitrary cross-sectional image, the diseased site and the like can be easily observed.

The case image search apparatus according to a third aspect of the present invention comprises: a cross-sectional image specifying device which specifies a first arbitrary cross-sectional image obtained by cutting a three-dimensional image to be diagnosed with a cutting plane arbitrarily positioned and angled; a first feature value calculating device which calculates a first feature value of a diseased site in the specified first arbitrary cross-sectional image; a database which stores a plurality of case images as three-dimensional images; a second cross-sectional image producing device which produces a second arbitrary cross-sectional image for each of the case images registered in the database based on the three-dimensional image of the case image, the second arbitrary cross-sectional image containing a diseased site and angled by the same amount as that specified by the cross-sectional image specifying device; a second feature value calculating device which calculates a second feature value of the diseased site in the second arbitrary cross-sectional image produced for each of the case images; and a searching device which compares the first feature value with the second feature value and searches the database for a case image having a second feature value similar to the first feature value.

It is intended that the database can be searched for a similar case based on the first feature value of a diseased site in an arbitrary cross-sectional image. That is, the database has registered a three-dimensional image of each case image, and an arbitrary cross-sectional image is produced from the three-dimensional image for each case image, the cross-sectional image containing a diseased site and angled by the same amount as that specified above (the angle of the arbitrary cross-sectional image). Then, the second feature value of the diseased site in each of the arbitrary cross-sectional images is calculated, and the database is searched for a case image having a second feature value similar to the first feature value.

According to a fourth aspect of the present invention, the case image search apparatus according to the third aspect further comprises: a first cross-sectional image producing device which produces a first arbitrary cross-sectional image from the three-dimensional image based on the specification by the cross-sectional image specifying device; a first displaying device which displays the produced first arbitrary cross-sectional image; and a second display device which displays the second arbitrary cross-sectional image produced by the second cross-sectional image producing device, the second arbitrary cross-sectional image corresponding to the case image searched for by the searching device. In this way, the second arbitrary cross-sectional image (case image to be referred to) angled by the same amount as the first arbitrary cross-sectional image to be diagnosed can be displayed.

According to a fifth aspect of the present invention, in the case image search apparatus according to the second or fourth aspect, a single display device functions as the first and second displaying devices, and the first and second arbitrary cross-sectional images are displayed at the same time or on separate screens.

According to a sixth aspect of the present invention, in the case image search apparatus according to the second aspect, a single display device functions as the first and second displaying devices, and the first arbitrary cross-sectional image, the second arbitrary cross-sectional image, and the produced cross-sectional image are displayed at the same time or on separate screens.

According to a seventh aspect of the present invention, in the case image search apparatus according to the second, fourth, fifth, or sixth aspect, the database stores case images along with diagnosis information for each of the case images, and the second displaying device displays the second arbitrary cross-sectional image along with the diagnosis information corresponding to the second arbitrary cross-sectional image.

In this way, the second arbitrary cross-sectional image (case image to be referred to) angled by the same amount as the first arbitrary cross-sectional image to be diagnosed along with the diagnosis information on the second arbitrary cross-sectional image can be displayed.

The eighth aspect of the present invention is a case image search system including a user terminal and a case image server connected to the user terminal via a network. The user terminal includes: a cross-sectional image specifying device which specifies an arbitrary cross-sectional image obtained by cutting a three-dimensional image to be diagnosed with a cutting plane arbitrarily positioned and angled; a cross-sectional image producing device which produces a cross-sectional image from the three-dimensional image with reference to a diseased site in the specified arbitrary cross-sectional image, the cross-sectional image oriented in an axial direction set in advance and containing the diseased site; a first feature value calculating device which calculates a first feature value of the diseased site contained in the produced cross-sectional image based on the cross-sectional image; and a first communication device which sends the calculated first feature value to the case image server and receives a case image searched for by the case image server. And, the case image server includes: a database which stores a plurality of case images and a second feature value of each of the case images which is associated with a case image, the second feature value for diseased site in a cross-sectional image oriented in the axial direction set in advance; a searching device which compares the first feature value with the second feature value and searches the database for a case image having a second feature value similar to the first feature value; and a second communication device which receives the first feature value from the user terminal and sends the searched case image to the user terminal.

The ninth aspect of the present invention is a case image search system including a user terminal and a case image server connected to the user terminal via a network. The user terminal includes: a cross-sectional image specifying device which specifies an arbitrary cross-sectional image obtained by cutting a three-dimensional image to be diagnosed with a cutting plane arbitrarily positioned and angled; a cross-sectional image producing device which produces a cross-sectional image from the three-dimensional image with reference to a diseased site in the specified arbitrary cross-sectional image, the cross-sectional image oriented in an axial direction set in advance and containing the diseased site; and a first communication device which sends the produced cross-sectional image to the case image server and receives a case image searched for by the case image server. And, the case image server includes: a feature value calculating device which calculates a first feature value of the diseased site in the produced cross-sectional image based on the cross-sectional image; a database which stores a plurality of case images and a second feature value of each of the case images which is associated with a case image, the second feature value for diseased site in a cross-sectional image oriented in the axial direction set in advance; a searching device which compares the first feature value with the second feature value and searches the database for a case image having a second feature value similar to the first feature value; and a second communication device which receives the reference cross-sectional image and sends the searched case image to the user terminal.

The tenth aspect of the present invention is a case image search system including a user terminal and a case image server connected to the user terminal via a network. The user terminal includes: a cross-sectional image specifying device which specifies an arbitrary cross-sectional image obtained by cutting a three-dimensional image to be diagnosed with a cutting plane arbitrarily positioned and angled; a feature value calculating device which calculates a first feature value of the diseased site contained in the specified arbitrary cross-sectional image based on the cross-sectional image; and a first communication device which sends the calculated first feature value and angular information on the specified arbitrary cross-sectional image to the case image server and receives a case image searched for by the case image server. And, the case image server includes: a database which stores a plurality of case images as three-dimensional images; a cross-sectional image producing device which produces an arbitrary cross-sectional image for each of the case images registered in the database based on the three-dimensional image of each of the case images, the cross-sectional image containing a diseased site and angled by the same amount as the specified arbitrary cross-sectional image; a second feature value calculating device which calculates a second feature value of the diseased site in the arbitrary cross-sectional image produced for each of the case images; a searching device which compares the first feature value with the second feature value and searches the database for a case image having a second feature value similar to the first feature value; and a second communication device which receives the calculated first feature value and the angular information on the specified arbitrary cross-sectional image from the user terminal and sends the searched case image to the user terminal.

The eleventh aspect of the present invention is a case image search system including a user terminal and a case image server connected to the user terminal via a network. The user terminal includes: a cross-sectional image specifying device which specifies an arbitrary cross-sectional image obtained by cutting a three-dimensional image to be diagnosed with a cutting plane arbitrarily positioned and angled; and a first communication device which sends the specified arbitrary cross-sectional image and angular information on the arbitrary cross-sectional image to the case image server and receives a case image searched for by the case image server. And, the case image server includes: a first feature value calculating device which calculates a first feature value of the diseased site in the specified arbitrary cross-sectional image based on the specified arbitrary cross-sectional image; a database which has registered a plurality of case images, each of which registered as a three-dimensional image; a cross-sectional image producing device which produces an arbitrary cross-sectional image for each of the case images registered in the database based on the three-dimensional image of each of the case images, the cross-sectional image containing a diseased site and angled by the same amount as the specified arbitrary cross-sectional image; a second feature value calculating device which calculates a second feature value of the diseased site in the arbitrary cross-sectional image produced for each of the case images; a searching device which compares the first feature value with the second feature value and searches the database for a case image having a second feature value similar to the first feature value; and a second communication device which receives the specified arbitrary cross-sectional image and the angular information on the specified arbitrary cross-sectional image from the user terminal and sends the searched case image to the user terminal.

According to the present invention, a desired arbitrary cross-sectional image in which a diseased site and the like is easily observed can be selected, and case images registered in a database can be searched for a similar case image based on the arbitrary cross-sectional image.

BRIEF DESCRIPTION OF THE DRAWINGS

FIG. 6 shows examples of shape classification;

FIG. 7 shows the relationship between the shape classification, the second moment and the circularity;

FIG. 10 is a flowchart showing the processes performed on the case image server side;

FIG. 11 a table showing an example of first feature value data extracted from a query image;

FIG. 12 is a table showing an example of second feature value data stored in a feature value DB for each case image classified in terms of disease;

FIGS. 16A and 16B show how an MPR image angled by the same amount as a query image (MPR image) is produced in the case image server.

DETAILED DESCRIPTION OF THE PREFERRED EMBODIMENTS

Preferred embodiments of the case image search apparatus and system according to the present invention will be described below with reference to the accompanying drawings.

<System Configuration>

Figure 1:
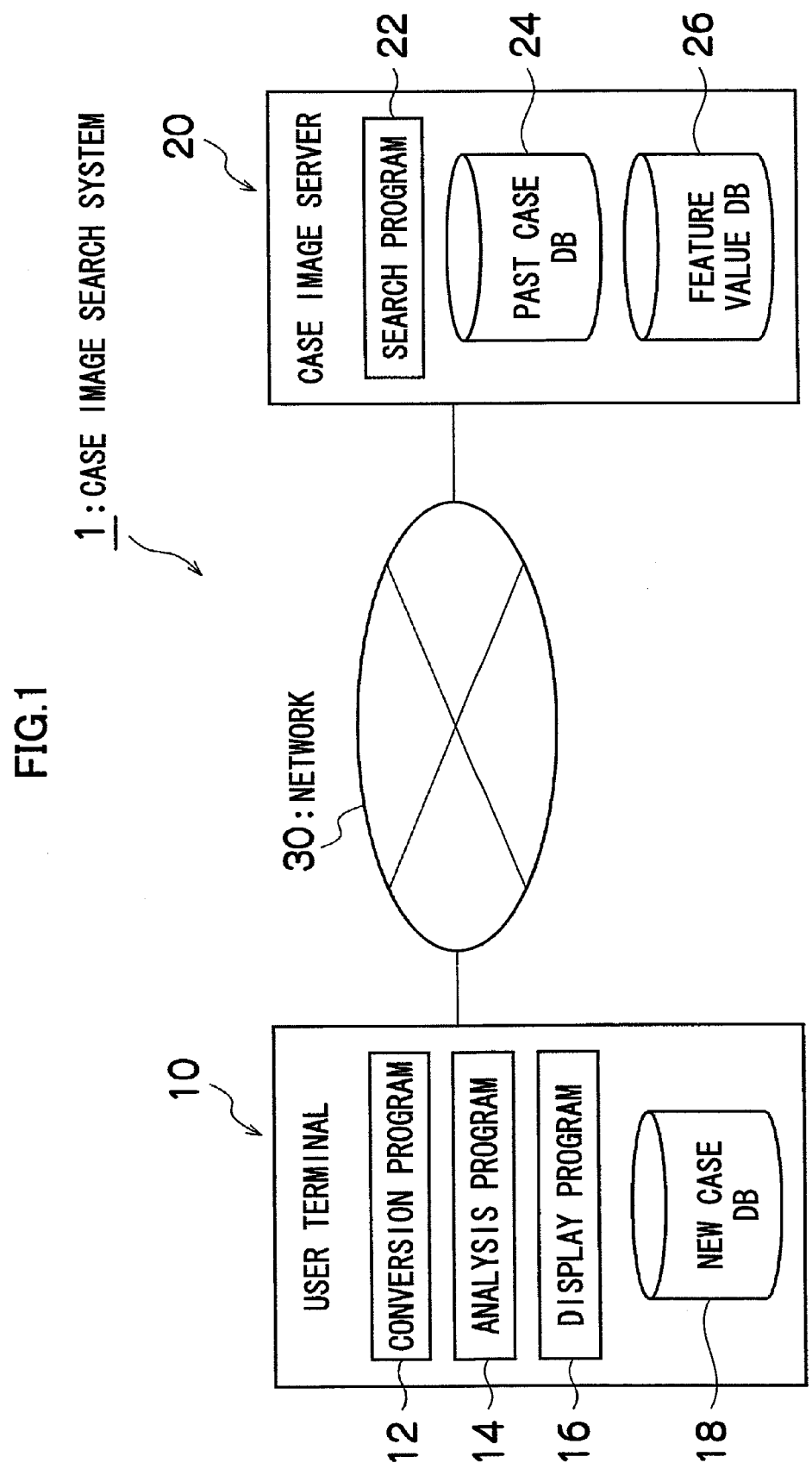
FIG. 1 is a system configuration diagram showing an embodiment of the case image search system according to present invention.

FIG. 1 is a system configuration diagram showing an embodiment of the case image search system according to present invention.

The case image search system 1 includes a user terminal 10, a case image server 20, and a network 30 for connecting them to each other.

The user terminal 10 includes a personal computer connected to the network 30, and the main part of the computer includes a conversion program 12, an analysis program 14, a display program 16, an operation section, such as a keyboard and a mouse, a monitor, and a new case database (DB) 18.

The new case database DB 18 stores three-dimensional images of new patients to be diagnosed. Each of the three-dimensional images is captured, for example, with an X-ray CT scanner, and is formed of tomograms (axial images) perpendicular to the body axis direction of the subject and successively arranged along the body axis direction.

A user can use the keyboard and mouse to arbitrarily specify the position and angle of the cutting plane used to cut a three-dimensional image to be diagnosed. The user terminal 10 can produce an arbitrary cross-sectional image obtained by cutting the three-dimensional image to be diagnosed with the thus specified cutting plane arbitrarily positioned and angled (hereinafter referred to as "MPR (Multi Planner Reconstruction) image") and display the MPR image on the monitor.

That is, the user can operate the user terminal 10 to display a desired MPR image on the monitor for image diagnosis.

The conversion program 12 converts the MPR image specified by the user and containing a diseased site into an axial image passing through a predetermined point in the diseased site used. The axial image is used as a query.

From the query image (axial image), the analysis program 14 calculates feature values (first feature values) of the diseased site in the axial image. There are a number of types of feature values of a diseased site, such as the shape, size, and concentration of the diseased site.

The display program 16 displays the MPR image, the axial image, the result of a query to the case image server 20 (a case image (MPR image) and diagnosis information to be referred to) and the like on the monitor.

The main part of the case image server 20 includes a search program 22, a case DB 24, and a feature value DB 26.

The search program 22 searches the case DB 24 and the feature value DB 26 for relevant information in response to a search request from the user and sends the search result to the user terminal.

The case DB 24 stores case information to be searched for on a disease basis. The case information includes a case image (three-dimensional image) of a definitely diagnosed disease and diagnosis information in the form of text, such as a radiogram interpretation report created by a radiogram interpreter and diagnosis descriptions created by a clinician for the case image.

The feature value DB 26 stores feature values (second feature values) of the diseased site in each of the case images for each disease. The second feature values are calculated for the diseased site in an axial image passing through a predetermined point in the diseased site.

<Inputting a Case Image>

Figure 2:
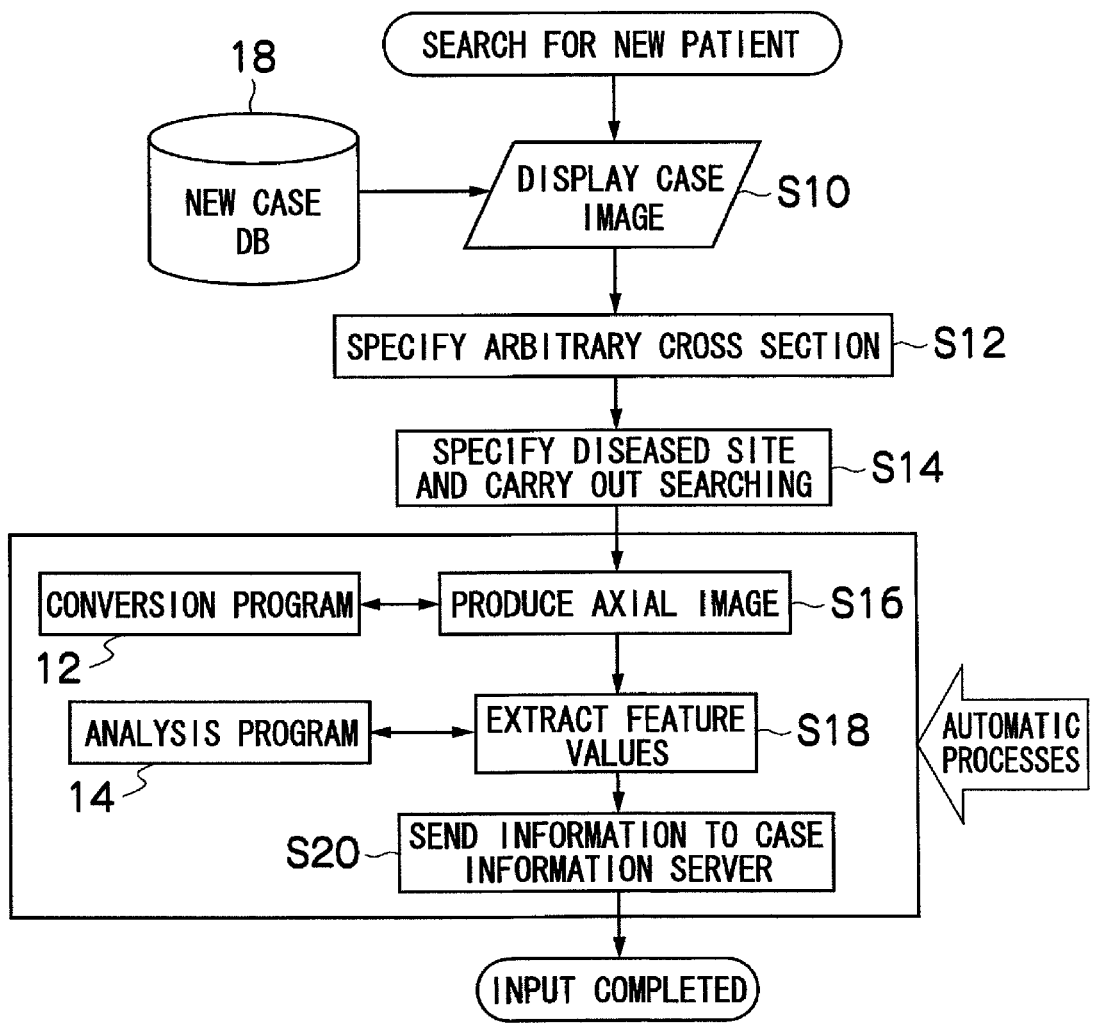
FIG. 2 is a flowchart showing the processes performed on the user terminal side.

FIG. 2 is a flowchart showing the processes performed on the user terminal side.

The user searches the new case DB 18 for an image of a new patient, and displays a case image (MPR image) to be diagnosed on the monitor of the user terminal 10 (step S10). To display the MPR image, the user specifies an arbitrary cross section (arbitrarily positioned and angled cutting plane used to cut the three-dimensional image) so that an MPR image in which the diseased site is easily observed is displayed (step S12).

Figure 3:
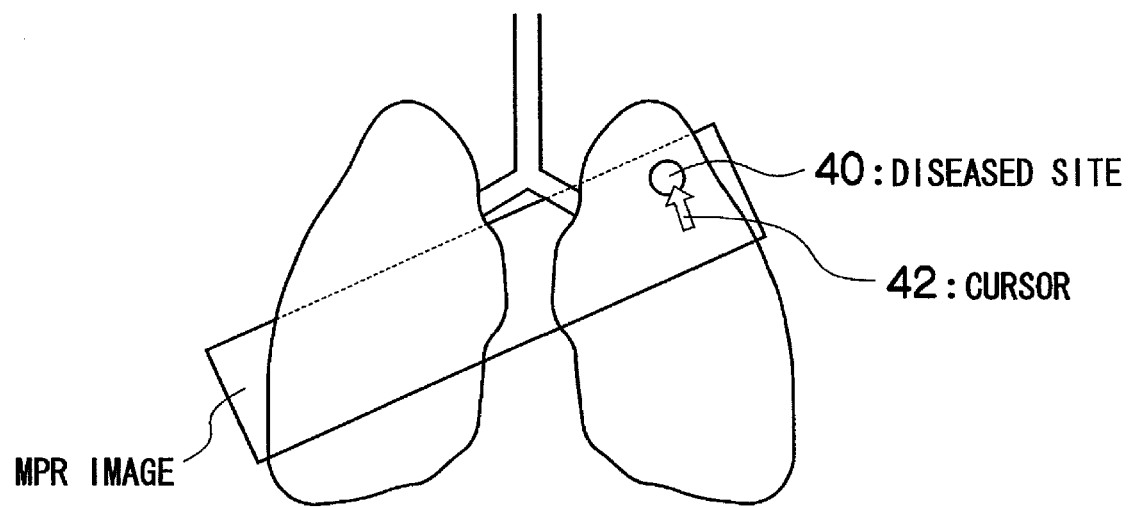
FIG. 3 explains how to specify a disease site in an MPR image.

Then, the user diagnoses the MPR image displayed on the monitor. Specifically, as shown in FIG. 3, the user uses the mouse or the like to move a cursor 42 to a diseased site 40 in the MPR image, marks the diseased site in a one-click 3D measurement process, and carries out searching (step S14).

Figure 4D:
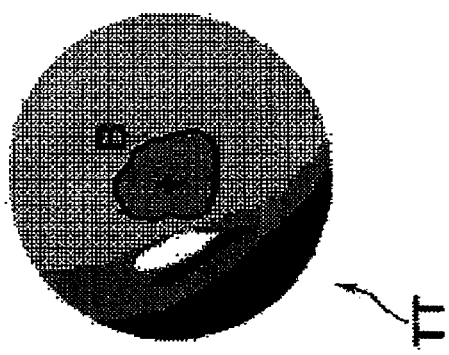
FIGS. 4A to 4D explain how to automatically extract the diseased site (region of interest)
Figure 4C:
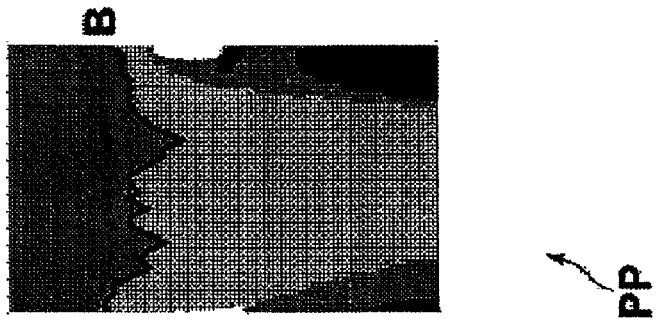
Figure 4B:
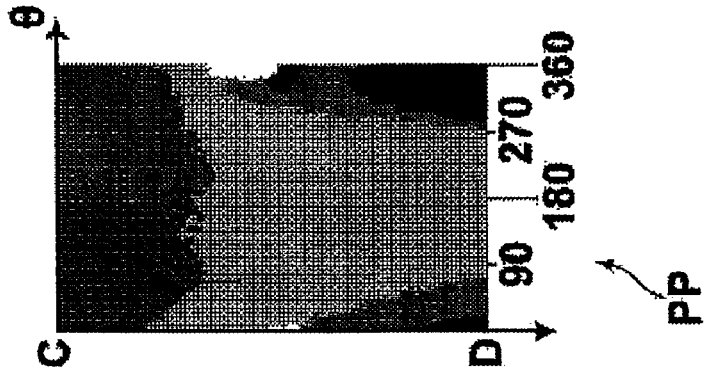
Figure 4A:
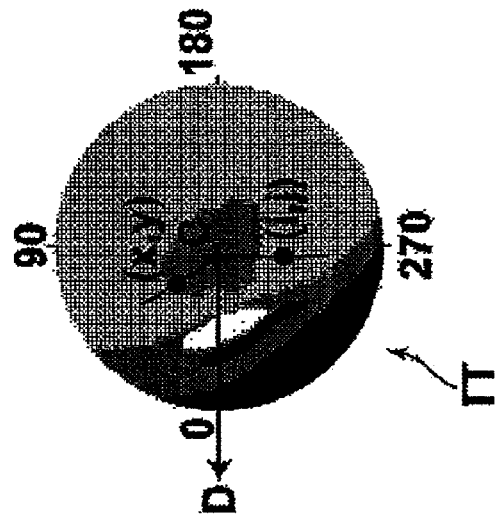

The one-click 3D measurement will be made on the diseased site 40 in the following manner:

First, as shown in FIG. 4A, a diseased site (tumor region) around a specified point C is extracted. The specified point C is desirably a point close to the center of the tumor region.

A fixed-radius area containing an adequate part of the tumor region is determined as a judgment area TT.

Then, the image of the judgment area TT as shown in FIG. 4A is converted into a judgment image PP by unfolding the image of the judgment area TT onto a polar-coordinate plane expressed by the distance from the point C and the angle $\theta$ with respect to a predetermined line passing through the point C. For example, the polar-coordinate image in FIG. 4B, which is obtained by performing polar-coordinate conversion expressed by the angle $\theta$ in the clockwise direction with reference to the radial line segment CD in the image in FIG. 4A, is used to judge whether or not each pixel in the judgment area is the contour of the tumor region.

Based on a feature value L extracted from brightness information in the one-dimensional brightness profile on the line passing through each pixel (x, y) in the judgment area and the point C, an evaluation value S indicative of whether or not each pixel (x, y) in the judgment area represents the contour is calculated.

The brightness value in the one-dimensional brightness profile on the line passing through each pixel (x, y) and the point C shows abrupt changes on opposite sides of the contour of the tumor region. Bearing this fact in mind, a feature value is calculated from each brightness value, and a discriminator using the feature value is prepared. The result obtained from the discriminator provides an image (x, y) that forms the contour indicated by the thick line B in FIG. 4C. Then, the judgment area PP expressed in the polar-coordinate system is inversely converted into the one expressed in the orthogonal coordinate system, so that the contour in the image of the judgment area TT is determined as shown in FIG. 4D. The area surrounded by the contour is extracted as the tumor region (that is, the region of interest).

Alternatively, the region of interest may be extracted by using an area separation method described in, for example, Wormanns D, Kohl G, Klotz E et al., "Volu-metric measurements of pulmonary nodules at multi-row detector CT: in vivo reproducibility," Eur Radiol 2004; 14(1): pp. 86-92.

Referring back to FIG. 2, when receiving a search command, the conversion program 12 uses the three-dimensional image to be diagnosed along with the angle when the user specified the cross-section, the single point in the diseased site, and the 3D area separation information to produce an axial image passing through a predetermined single point in the diseased site (the axial image reflects the result of the separation of the diseased site area) (step S16). An example of the predetermined single point in the diseased site is the center of gravity of the diseased site area.

Figure 5B:
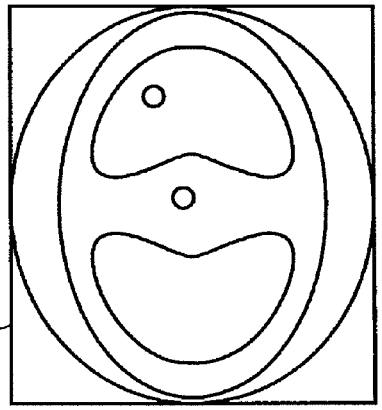
FIGS. 5A and 5B show how an axial image is produced from an MPR image.
Figure 5A:
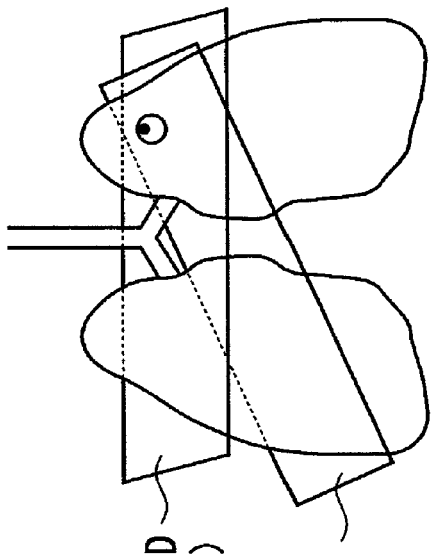

The thus produced axial image (FIG. 5B) is used as an actual query image in the system.

After the axial image has been produced, the axial image is transferred to the analysis program 14, which determines feature values (first feature values) from the axial image (step S18).

The first feature values are extracted as follows:

The analysis program 14 analyzes features of the extracted region of interest (diseased site).

When the region of interest includes abnormal shadows that appear in the lung field, such as tumors and pulmonary nodules, each of the abnormal shadows presents features in shape, size, and concentrations in the edge portion of the region of interest and in the region of interest. The anatomical position where each of the abnormal shadows appears is also considered as one of the characteristics of the abnormal shadow. The region of interest is analyzed to determine the features in terms of shape, size, concentration in the region of interest, concentration in the edge portion of the region of interest, the anatomical positions, and the like.

(1) Feature in Shape

The shape of an abnormal shadow can be classified into quasi-circles, lobular shapes, polygons, stars, spicular shapes, sawtooth shapes, and irregular shapes (for further details, see Iwano et al., "Computer-aided diagnosis for discrimination of malignant from benign solitary pulmonary nodules," JRC2006, for example).

These shapes can be classified in terms of the circularity (ratio of the perimeter to the area) and the second moment of the center of gravity (the sum of the squares of the distance between the center of gravity of the nodule and a pixel in the nodule normalized by the square of the area).

The distribution of the circularity and the second moment shown in FIG. 7 is classified into quasi-circles, lobular shapes, polygons, stars, spicular shapes, sawtooth shapes, and irregular shapes (those that do not belong to any of the preceding classifications) represented by respective elliptical areas. Then, an existing non-linear discriminant analysis, design discriminant analysis or the like can be used to achieve a discriminator that receives inputs of feature values, such as the circularity and the second-order moment, and outputs the shape of an abnormal shadow of interest.

(2) Feature in Size

The size of an abnormal shadow is expressed, for example, by the area, volume, and the lengths of the major and minor axes, and can be automatically measured from the region of interest extracted by the extraction device 43 described above.

(3) Feature in Concentration in the Region of Interest

Abnormal shadows are classified in terms of concentration into Pure GGO (ground-glass opacity), Mixed GGO (ground-glass opacity and high concentration), and Solid (high concentration). The discrimination can be carried out by using an existing non-linear discriminant analysis, design discriminant analysis or the like along with the average, deviation, maximum, and minimum of the concentration in the region of interest extracted by the extraction device 43 described above as the feature values.

Further, the concentration value can be used to classify abnormal shadow areas in terms of whether or not there is a calcified portion, or there is a cavity. It is judged that there is a calcified portion when the maximum concentration in the region of interest is greater than or equal to a certain threshold value (as a guideline, for example, a CT value of 500). It is judged that there is a cavity when the minimum concentration in the region of interest is smaller than or equal to a certain threshold value (as a guideline, for example, a CT value of 500).

(4) Feature in Concentration in the Edge Portion of the Region of Interest

Figure 8A:
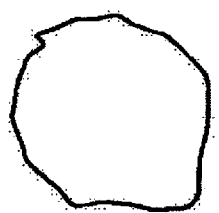
FIGS. 8A and 8B show a region of interest and its surrounding area.
Figure 8B:
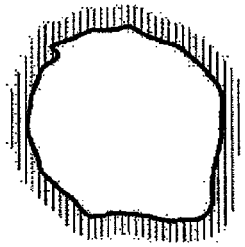

The edge of an abnormal shadow can be classified in terms of whether or not it is clear. Classification in terms of whether or not the edge is clear is carried out by using the difference in concentration between the inside and outside of the contour of the region of interest extracted by the analysis program 14. For the region of interest, the contour of which is indicated by the thick line shown in FIGS. 8A and 8B, the difference in concentration is determined by substituting the concentration values in the inner area (inside the contour) and the surrounding area (the hatched portion outside the contour in FIG. 8B) into the following equation.

$$\text{Difference in concentration} = [\text{average concentration (surrounding area)} - \text{average concentration (inner area)}] / [\text{variance (surrounding area)} + \text{variance (inner area)}]$$

(5) Anatomical Positions

Figure 9B:
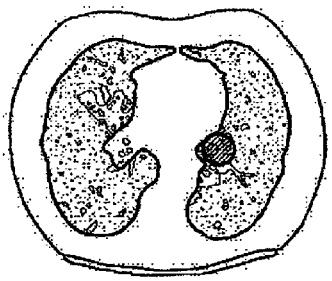
FIGS. 9A to 9E explain how to analyze an anatomical position in a chest image.
Figure 9C:
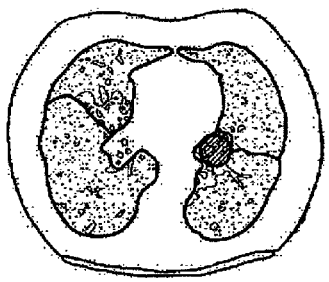
Figure 9A:
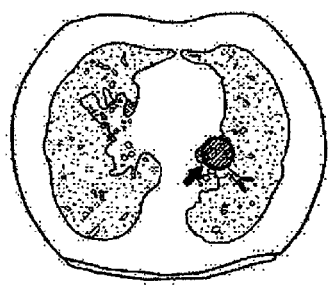
Figure 9D:
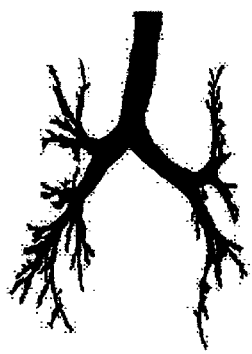
Figure 9E:
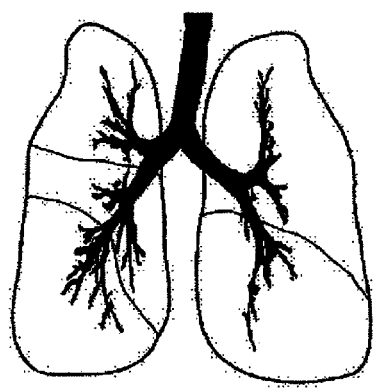

Next, the anatomical position of the region of interest is recognized. For example, in a chest image, as shown in FIGS. 9A to 9E, the lung field (see FIG. 9B) and the bronchus (FIG. 9D) are automatically extracted from an input chest image (see FIG. 9A). Then, the shape of the bronchus is used to extract interlobar fissures (see FIGS. 9C and 9E) and perform lung lobe classification to divide and classify the lung field (upper right lobe, middle right lobe, lower right lobe, upper left lobe, and lower left lobe) (for further details, see, for example, Document 1: Tatsuro Hayashi, Xiangrong Zhou, Takeshi Hara, Hiroshi Fujita, Ryujiro Yokoyama, Takuji Kiryu, and Hiroaki Hoshi, "Development of the Procedure for Automatic Extracting Interlobar Fissures and its Performance Evaluation," the Institute of Electronics, Information and Communication Engineers, Technical Report, MI2003-53, pp. 39-44, 2003, Document 2: Nakada, et al., "Study on lobe classification of the bronchus extracted from three-dimensional chest CT images," 15th Conference of Japan Society of Computer Aided Diagnosis of Medical Images, pp. 275-276, November, 2005, Document 3: Tanaka, et al., "Automated Classification of Pulmonary Artery and Vein from Chest X-ray CT Images Based on Spatial Arrangement Features of Bronchus and Vessels," the transactions of the Institute of Electronics, Information and Communication Engineers, D-II, Vol. J88, pp. 1421-1431, April, 2005, and Document 4: Shyu C, Brodley C E, Kak A, Kosaka A, Aisen A, and Broderick L, ASSERT, "A physician-in-the-loop content-based image retrieval system for HRCT image databases," Computer Vision and Image Understanding, 1999; 74: pp. 111-132). For example, the anatomical position of the region of interest (the portion indicated by the black arrow) shown in FIG. 9A is recognized as "left lung/upper lobe/S2."

Referring back to FIG. 2, after the first feature values are extracted as described above, the first feature values and the information on the arbitrary cross section (angular and positional information) are sent to the case image server 20 (step S20).

The case image server 20 searches the case DB 24 in the server for a highly similar case image based on the above information.

<Searching for Cases>

The case image server 20 searches the past case feature value DB 26 for a case image highly similar to the query case based on the feature values received from the user terminal 10. When there is a relevant case, that case is used as the key to obtain detailed case information from the case DB 24.

FIG. 10 is a flowchart showing the processes performed on the case image server side.

The case image server 20 receives the first feature values and the information on the arbitrary cross section from the user terminal 10 (step S30).

Then, each of the first feature values of the query image are compared with the corresponding one of the second feature values in the feature value DB 26 for each case image to calculate the similarity between the first and second feature values (step S32).

FIG. 11 shows an example of first feature value data extracted from the query image, and FIG. 12 shows an example of second feature value data stored in the feature value DB 26 for each case image (A-001, A-002, . . . , B-001, B-002, . . . ) classified in terms of disease (A, B, . . . ).

In the step S32, based on the first feature values $m_i$ (i=1, 2, . . . , n) extracted from the query image and the second feature values $M_i$ (i=1, 2, . . . , n) of each case image, the similarity S between the query image and each case image is calculated by using the following equation:

$$S = \sum_{i=1}^{n} w_i |Mi - mi|$$ [Formula 1]

In the above formula 1, $w_i$ (i=1, 2, . . . , n) are weighting coefficients for each feature value defined in advance for each disease. As apparent from the formula 1, the closer to zero the calculated similarity S is, the higher the similarity between the query image and the case image becomes.

The similarity S is separately calculated for each disease.

Figure 13:
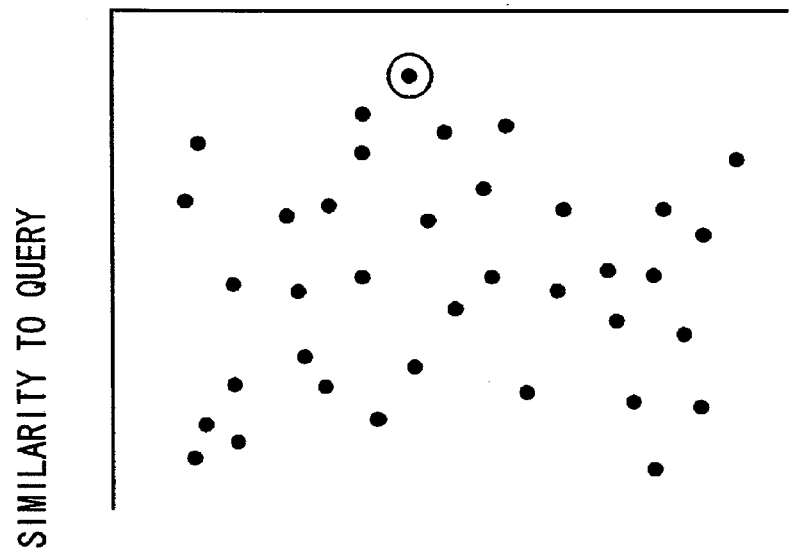
FIG. 13 is a graph obtained by plotting the similarity between each case image for each disease and the query image.

FIG. 13 is a graph obtained by plotting the similarity between each case image for a disease A and the query image. The horizontal axis represents each case, and the vertical axis represents the similarity. In FIG. 13, the circled case image most resembles the query image.

Referring back to FIG. 10, in the step S34, a case image having the highest similarity (representative case) is searched for on a disease basis.

The feature values of each case image registered in the feature value DB 26 are related to the case information registered in the case DB 24. Based on the case ID of the representative case having the highest similarity searched for on a disease basis in the step S34, the corresponding case information is retrieved from the case DB 24 (step S36).

The case information includes not only the image data but also diagnosis information in the form of text, such as test results including a radiogram interpretation report, an electronic chart, and definitive diagnosis information. These pieces of information are presented to the user in the following manner:

Case images to be presented include the axial image that has gone through similarity searching as well as the MPR image which passes through the diseased site in the axial image and is angled by the same amount as the new case MPR image.

That is, the case DB 24 stores three-dimensional images for each case, and the case image server 20 has a function of using any of the three-dimensional images to produce an MPR image that passes through a predetermined point in the diseased site based on the cross-section information (angular information) on the MPR image received from the user terminal 10. The produced MPR image is then presented to the user.

In this example, searching for a representative case having the highest similarity for each disease allows one image for a single disease to be searched for. However, by allowing a plurality of images to be searched for, similar images may be searched for in descending order of similarity.

<Displaying Similar Case Images>

When a similar case is searched for by carrying out the processes described above, the case image and associated information are presented to the user. To display the image, the method described in Japanese Patent Application Laid-Open No. 2001-101449 entitled, "THREE-DIMENSIONAL IMAGE DISPLAY APPARATUS" (TeraRecon, Incorporated) or the method described in the following section is used.

Figure 14:
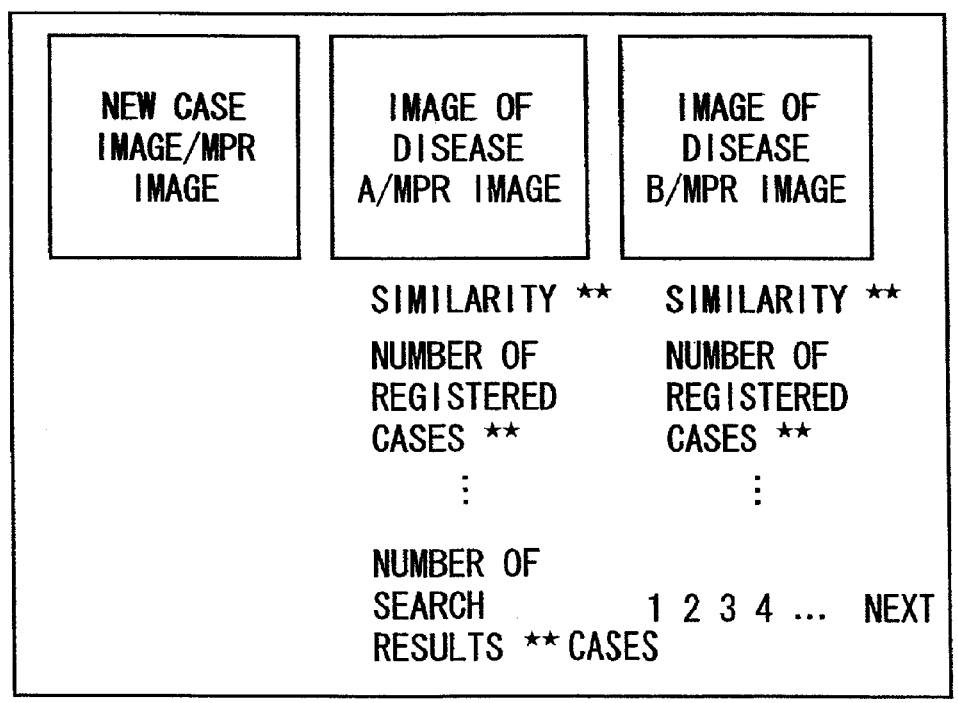
FIG. 14 shows an exemplary search display screen displayed on the monitor of the user terminal.

FIG. 14 shows an exemplary search display screen displayed on the monitor of the user terminal 10.

As shown in FIG. 14, the search display screen shows the new case image (MPR image) and representative cases (MPR images) for each disease similar to the query image.

The representative cases are presented in descending order of similarity. In FIG. 14, representative cases for a disease A and representative cases for a disease B are displayed. The screen also displays information including the similarity of each of the representative cases for each disease, the number of registered cases for each disease, and the number of search results (similar diseases). Further, the screen displays a software button, "next page", for displaying other representative cases that cannot be simultaneously displayed on the monitor screen.

The user can compare the new case image (MPR image) with the representative cases (MPR images) for each disease for image-based diagnosis.

Further, the search result screen shown in FIG. 14 can be changed to a detail information screen on which more detailed information can be displayed.

Figure 15B:
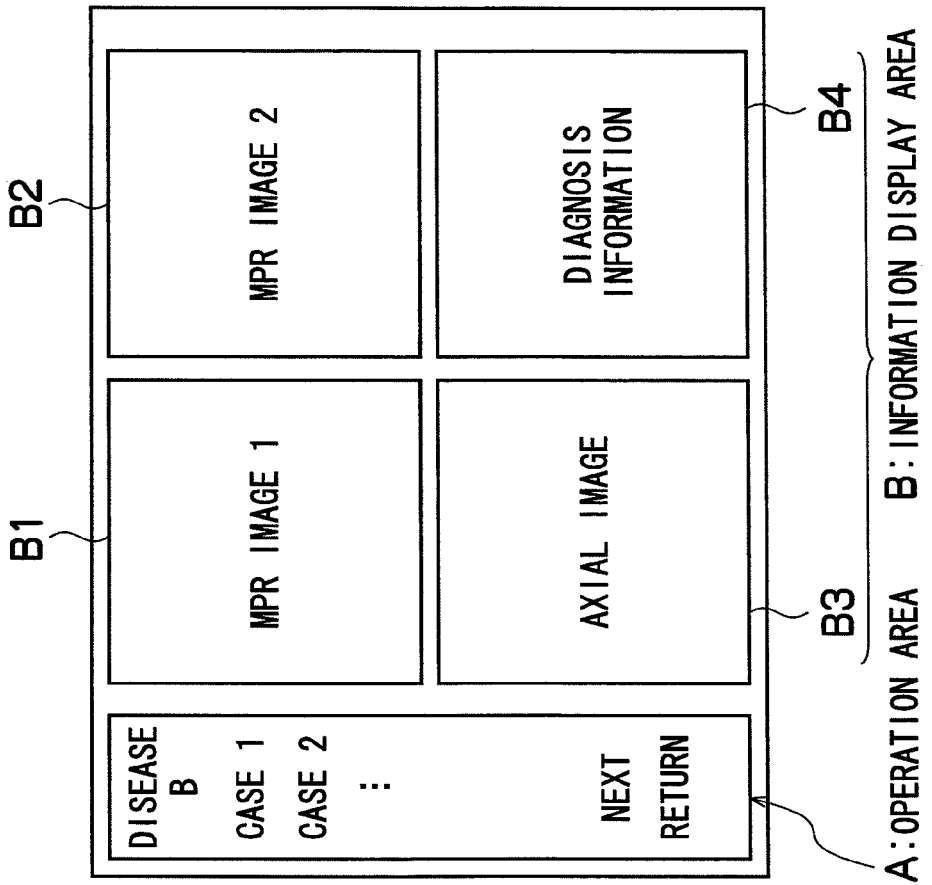
FIGS. 15A and 15B show an exemplary detailed information screen on which case information on a selected disease is displayed.
Figure 15A:
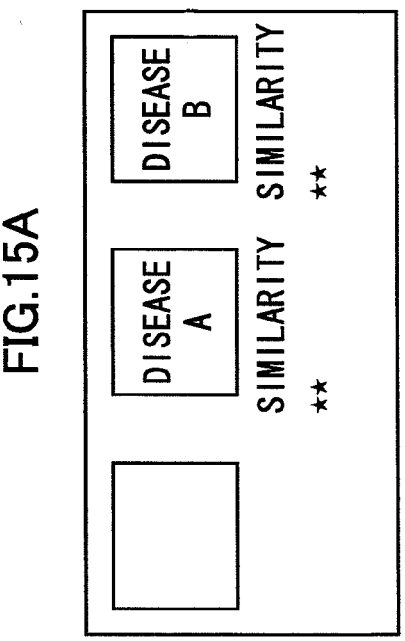

FIGS. 15A and 15B show an example of the detailed information screen on which case information on a selected disease is displayed.

FIG. 15A is the search result screen shown in FIG. 14, and FIG. 15B is the detailed information screen displayed by clicking any of representative cases for a specific disease on the search result screen. The detailed information screen shows detailed information on the selected disease.

As shown in FIG. 15B, the detailed information screen includes an operation area A on the left and an information display area B on the right.

The operation area A displays a list of cases for the disease selected in the search result screen (disease B, in this example) in descending order of similarity. By selecting a desired case from the list, detailed information on the selected case is displayed in the information display area B.

The information display area B is formed of four display areas B1 to B4. The display area B1 displays an MPR image 1 (MPR image angled by the same amount as the new case image (MPR image)). The display area B2 displays an MPR image 2 differently angled from the MPR image 1 (MPR image perpendicular to the MPR image 1, for example). The display area B3 displays an axial image containing a diseased site. The display area B4 displays diagnosis information in the form of text, such as a radiogram interpretation report and definitive diagnosis information.

Other Embodiments

In the above embodiment, although the user terminal 10 is configured to convert an MPR image into an axial image, uses the converted axial image as a query image to determine first feature values used for searching, and send the first feature values and the angular information on the MPR image to the case image server 20, the invention is not limited thereto. An MPR image may be used as the query image to determine first feature values used for searching, and the first feature values and the angular information on the MPR image may be sent to the case image server 20.

When an MPR image is used as the query image, the case image server 20 produces an MPR image angled by the same amount as the query image and passing through a specific point in the diseased site for each case as shown in FIGS. 16A and 16B. After the MPR image has been produced, feature values (second feature values) are calculated from the MPR image.

Then, each of the first feature values received from the user terminal 10 is compared with the corresponding one of the calculated second feature values to calculate the similarity between the first and second feature values for each case. Based on the calculation result, a case image (MPR image) similar to the query image (MPR image) is searched for. The case image server 20 sends the thus searched case image (MPR image) and the like to the user terminal 10.

<Variation>

Although the conversion program in the user terminal is configured to convert an MPR image into an axial image, the MPR image is not necessarily converted into an axial image but a cross-sectional image oriented in an axial direction set in advance, such as a coronal image and a sagittal image. In this case, the case image server needs to hold feature values of a diseased site in a cross-sectional image of the same type as the cross-sectional image converted in the user terminal.

In the above embodiment, although the user terminal is configured to send first feature values calculated from a query image to the case image server, the query image itself may be sent and the case image server may calculate feature values to be used for searching (first feature values) from the received query image.

Further, the network 30 shown in FIG. 1 may be a secure network external to the system, such as IPSec and SSL-VPN, or may be an internal network, such as an intra-LAN.

The invention is applicable to not only a network-based case image search system but also a stand-alone case image search apparatus that performs all processes therein.

What is claimed is:

1. A case image search apparatus comprising:
   a cross-sectional image specifying device which specifies an arbitrary cross-sectional image obtained by cutting a three-dimensional image to be diagnosed with a cutting plane arbitrarily positioned and angled;
   a cross-sectional image producing device which produces a cross-sectional image from the three-dimensional image with reference to a diseased site in the specified arbitrary cross-sectional image, the cross-sectional image oriented in an axial direction set in advance and containing the diseased site;
   a feature value calculating device which calculates a first feature value of the diseased site contained in the produced cross-sectional image based on the cross-sectional image;
   a database which stores a plurality of case images and a second feature value of each of the case images, which is associated with a case image, the second feature value for diseased site in a cross-sectional image oriented in the axial direction set in advance; and
   a searching device which compares the first feature value with the second feature value and searches the database for a case image having a second feature value similar to the first feature value.

2. The case image search apparatus according to claim 1, wherein
   the database stores each of the case images as a three-dimensional image,
   the case image search apparatus, further comprises:
   a first cross-sectional image producing device which produces a first arbitrary cross-sectional image from the three-dimensional image based on the specification by the cross-sectional image specifying device;
   a first displaying device which displays the produced first arbitrary cross-sectional image;
   a second cross-sectional image producing device which produces a second arbitrary cross-sectional image from the three-dimensional image corresponding to the case image searched for by the searching device, the second arbitrary cross-sectional image containing a diseased site and angled by the same amount as that specified by the cross-sectional image specifying device; and
   a second display device which displays the produced second arbitrary cross-sectional image.

3. The case image search apparatus according to claim 2, wherein a single display device functions as the first and second displaying devices, and the first and second arbitrary cross-sectional images are displayed at the same time or on separate screens.

4. The case image search apparatus according to claim 2, wherein
   the database stores case images along with diagnosis information for each of the case images, and
   the second displaying device displays the second arbitrary cross-sectional image along with the diagnosis information corresponding to the second arbitrary cross-sectional image.

5. A case image search apparatus comprising:
   a cross-sectional image specifying device which specifies a first arbitrary cross-sectional image obtained by cutting a three-dimensional image to be diagnosed with a cutting plane arbitrarily positioned and angled;
   a first feature value calculating device which calculates a first feature value of a diseased site in the specified first arbitrary cross-sectional image;
   a database which stores a plurality of case images as three-dimensional images;
   a second cross-sectional image producing device which produces a second arbitrary cross-sectional image for each of the case images registered in the database based on the three-dimensional image of the case image, the second arbitrary cross-sectional image containing a diseased site and angled by the same amount as that specified by the cross-sectional image specifying device;
   a second feature value calculating device which calculates a second feature value of the diseased site in the second arbitrary cross-sectional image produced for each of the case images; and
   a searching device which compares the first feature value with the second feature value and searches the database for a case image having a second feature value similar to the first feature value.

6. The case image search apparatus according to claim 5, further comprising:
   a first cross-sectional image producing device which produces a first arbitrary cross-sectional image from the three-dimensional image based on the specification by the cross-sectional image specifying device;
   a first displaying device which displays the produced first arbitrary cross-sectional image; and
   a second display device which displays the second arbitrary cross-sectional image produced by the second cross-sectional image producing device, the second arbitrary cross-sectional image corresponding to the case image searched for by the searching device.

7. The case image search apparatus according to claim 6, wherein a single display device functions as the first and second displaying devices, and the first and second arbitrary cross-sectional images are displayed at the same time or on separate screens.

8. The case image search apparatus according to claim 2, wherein a single display device functions as the first and second displaying devices, and the first arbitrary cross-sectional image, the second arbitrary cross-sectional image, and the produced cross-sectional image are displayed at the same time or on separate screens.

9. The case image search apparatus according to claim 6, wherein
the database stores case images along with diagnosis information for each of the case images, and
the second displaying device displays the second arbitrary cross-sectional image along with the diagnosis information corresponding to the second arbitrary cross-sectional image.

10. A case image search system comprising a user terminal and a case image server connected to the user terminal via a network,
the user terminal including:
a cross-sectional image specifying device which specifies an arbitrary cross-sectional image obtained by cutting a three-dimensional image to be diagnosed with a cutting plane arbitrarily positioned and angled;
a cross-sectional image producing device which produces a cross-sectional image from the three-dimensional image with reference to a diseased site in the specified arbitrary cross-sectional image, the cross-sectional image oriented in an axial direction set in advance and containing the diseased site;
a first feature value calculating device which calculates a first feature value of the diseased site contained in the produced cross-sectional image based on the cross-sectional image; and
a first communication device which sends the calculated first feature value to the case image server and receives a case image searched for by the case image server, and
the case image server including:
a database which stores a plurality of case images and a second feature value of each of the case images which is associated with a case image, the second feature value for diseased site in a cross-sectional image oriented in the axial direction set in advance;
a searching device which compares the first feature value with the second feature value and searches the database for a case image having a second feature value similar to the first feature value; and
a second communication device which receives the first feature value from the user terminal and sends the searched case image to the user terminal.

11. A case image search system comprising a user terminal and a case image server connected to the user terminal via a network,
the user terminal including:
a cross-sectional image specifying device which specifies an arbitrary cross-sectional image obtained by cutting a three-dimensional image to be diagnosed with a cutting plane arbitrarily positioned and angled;
a cross-sectional image producing device which produces a cross-sectional image from the three-dimensional image with reference to a diseased site in the specified arbitrary cross-sectional image, the cross-sectional image oriented in an axial direction set in advance and containing the diseased site; and
a first communication device which sends the produced cross-sectional image to the case image server and receives a case image searched for by the case image server, and
the case image server including:
a feature value calculating device which calculates a first feature value of the diseased site in the produced cross-sectional image based on the cross-sectional image;
a database which stores a plurality of case images and a second feature value of each of the case images which is associated with a case image, the second feature value for diseased site in a cross-sectional image oriented in the axial direction set in advance;
a searching device which compares the first feature value with the second feature value and searches the database for a case image having a second feature value similar to the first feature value; and
a second communication device which receives the reference cross-sectional image and sends the searched case image to the user terminal.

12. A case image search system comprising a user terminal and a case image server connected to the user terminal via a network,
the user terminal including:
a cross-sectional image specifying device which specifies an arbitrary cross-sectional image obtained by cutting a three-dimensional image to be diagnosed with a cutting plane arbitrarily positioned and angled;
a feature value calculating device which calculates a first feature value of the diseased site contained in the specified arbitrary cross-sectional image based on the cross-sectional image; and
a first communication device which sends the calculated first feature value and angular information on the specified arbitrary cross-sectional image to the case image server and receives a case image searched for by the case image server, and
the case image server including:
a database which stores a plurality of case images as three-dimensional images;
a cross-sectional image producing device which produces an arbitrary cross-sectional image for each of the case images registered in the database based on the three-dimensional image of each of the case images, the cross-sectional image containing a diseased site and angled by the same amount as the specified arbitrary cross-sectional image;
a second feature value calculating device which calculates a second feature value of the diseased site in the arbitrary cross-sectional image produced for each of the case images;
a searching device which compares the first feature value with the second feature value and searches the database for a case image having a second feature value similar to the first feature value; and
a second communication device which receives the calculated first feature value and the angular information on the specified arbitrary cross-sectional image from the user terminal and sends the searched case image to the user terminal.

13. A case image search system comprising a user terminal and a case image server connected to the user terminal via a network, the user terminal including:

a cross-sectional image specifying device which specifies an arbitrary cross-sectional image obtained by cutting a three-dimensional image to be diagnosed with a cutting plane arbitrarily positioned and angled; and a first communication device which sends the specified arbitrary cross-sectional image and angular information on the arbitrary cross-sectional image to the case image server and receives a case image searched for by the case image server, and the case image server including:

a first feature value calculating device which calculates a first feature value of the diseased site in the specified arbitrary cross-sectional image based on the specified arbitrary cross-sectional image;

a database which stores a plurality of case images as three-dimensional images;

a cross-sectional image producing device which produces an arbitrary cross-sectional image for each of the case images registered in the database based on the three-dimensional image of each of the case images, the cross-sectional image containing a diseased site and angled by the same amount as the specified arbitrary cross-sectional image;

a second feature value calculating device which calculates a second feature value of the diseased site in the arbitrary cross-sectional image produced for each of the case images;

a searching device which compares the first feature value with the second feature value and searches the database for a case image having a second feature value similar to the first feature value; and a second communication device which receives the specified arbitrary cross-sectional image and the angular information on the specified arbitrary cross-sectional image from the user terminal and sends the searched case image to the user terminal.

* * * * *